United States Patent
Tosatti et al.

(10) Patent No.: US 11,623,026 B2
(45) Date of Patent: Apr. 11, 2023

(54) DEVICE HAVING A SWITCHABLE WET-DRY LUBRICATING COATING

(71) Applicant: SUSOS AG, Duebendorf (CH)

(72) Inventors: Samuele Tosatti, Duebendorf (CH); Olof Sterner, Zurich (CH); Stefan Zuercher, Zurich (CH); Christian Mathis, Zurich (CH)

(73) Assignee: SUSOS AG, Duebendorf (CH)

(*) Notice: Subject to any disclaimer, the term of this patent is extended or adjusted under 35 U.S.C. 154(b) by 133 days.

(21) Appl. No.: 16/615,680

(22) PCT Filed: May 30, 2017

(86) PCT No.: PCT/EP2017/063019
§ 371 (c)(1),
(2) Date: Nov. 21, 2019

(87) PCT Pub. No.: WO2018/219433
PCT Pub. Date: Dec. 6, 2018

(65) Prior Publication Data
US 2020/0086008 A1 Mar. 19, 2020

(51) Int. Cl.
*A61K 8/898* (2006.01)
*A61K 8/02* (2006.01)
*A61Q 5/06* (2006.01)
*A61L 27/52* (2006.01)
*A61L 27/34* (2006.01)
*A61L 29/08* (2006.01)
*A61L 29/14* (2006.01)

(52) U.S. Cl.
CPC .............. *A61L 27/52* (2013.01); *A61L 27/34* (2013.01); *A61L 29/085* (2013.01); *A61L 29/145* (2013.01); *A61L 2400/10* (2013.01)

(58) Field of Classification Search
CPC ..................................................... A61L 29/14
See application file for complete search history.

(56) References Cited

U.S. PATENT DOCUMENTS

| 4,838,876 | A | 6/1989 | Wong et al. |
| 5,639,810 | A | 6/1997 | Smith, III et al. |
| 2002/0068180 | A1* | 6/2002 | Yang ............... A61M 25/10 428/447 |
| 2008/0300554 | A1* | 12/2008 | Yafuso ............. A61L 29/085 523/121 |
| 2018/0163152 | A1* | 6/2018 | Luo ................. C10M 177/00 |

FOREIGN PATENT DOCUMENTS

| EP | 0 483 941 A2 | 5/1992 |
| EP | 2 236 524 A1 | 10/2010 |
| WO | 92/13718 A1 | 8/1992 |
| WO | 98/58690 A2 | 12/1998 |
| WO | 00/30696 A1 | 6/2000 |
| WO | 2006/037321 A1 | 4/2006 |
| WO | 2014/012080 A1 | 1/2014 |
| WO | 2014/209441 A2 | 12/2014 |

OTHER PUBLICATIONS

Sterner et al.; "Friction Measurements on Contact Lenses in a Physiologically Relevant Environment: Effect of Testing Conditions on Friction;" Investigative Ophthalmology & Visual Science; Oct. 2016; pp. 5383-5392; vol. 57, No. 13.
Feb. 22, 2018 Search Report issued in International Patent Application No. PCT/EP2017/063019.
Feb. 22, 2018 Written Opinion of the International Searching Authority issued in International Patent Application No. PCT/EP2017/063019.
Mar. 2, 2021 Office Action issued in Japanese Patent Application No. 2019-565803.

* cited by examiner

*Primary Examiner* — Kyle A Purdy
(74) *Attorney, Agent, or Firm* — Oliff PLC

(57) ABSTRACT

A lubricating coating including at least one polymer A, a cross-linker and at least one lubricating agent, and wherein a portion of the at least two reactive groups of the cross-linker are covalently linked to the polymer A to form a three-dimensional network in which the lubricant is incorporated, and wherein at the same time another portion of the reactive groups of the cross-linker are covalently linked to the surface of the device or to the optional adhesion layer on the surface of the device.

21 Claims, 4 Drawing Sheets

Figure 1:
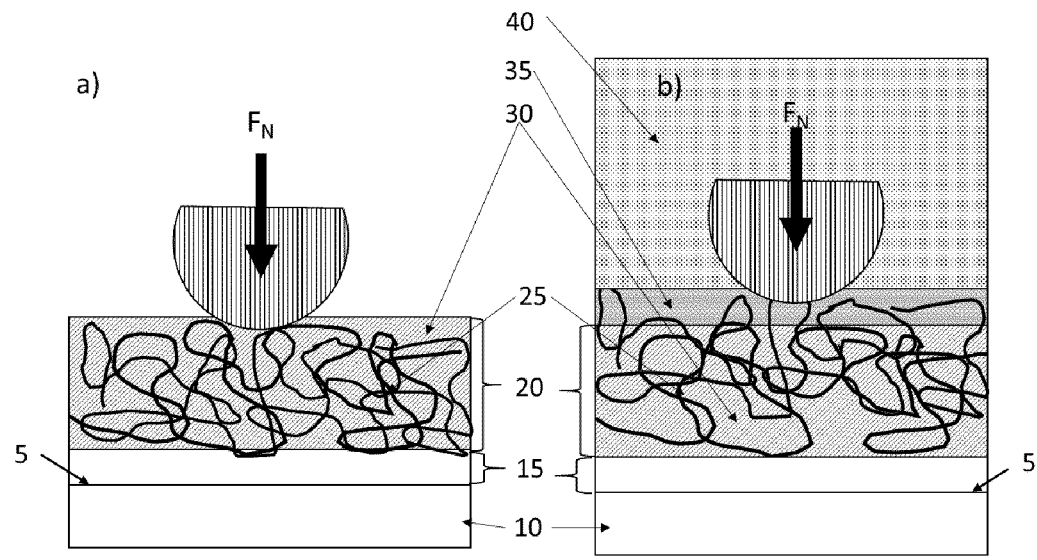

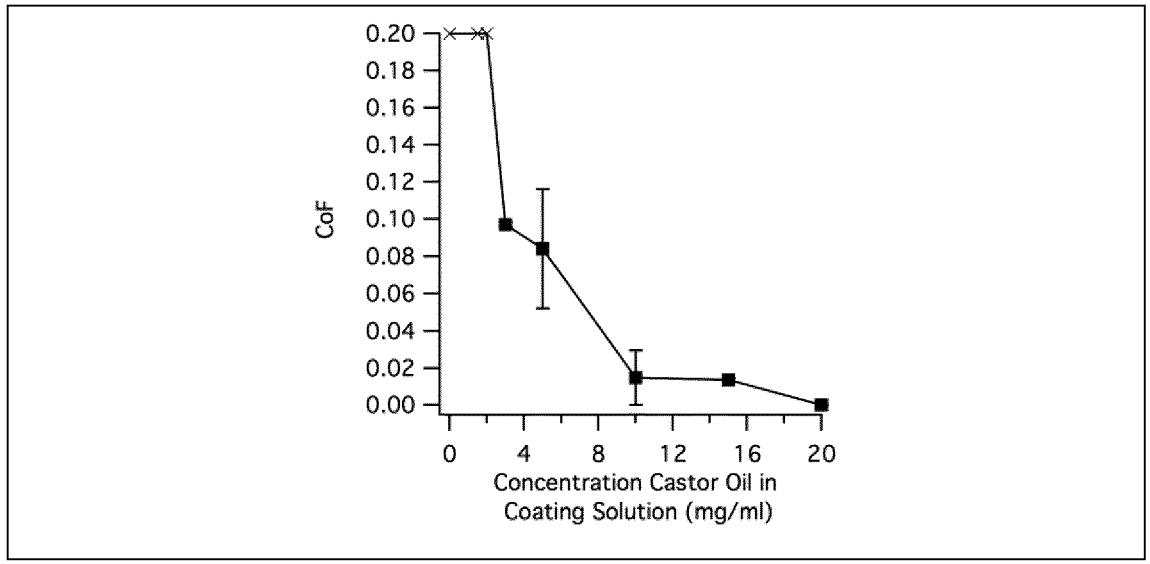
Figure 3: Coefficient of friction as a function of castor oil concentration in the coating formulation.
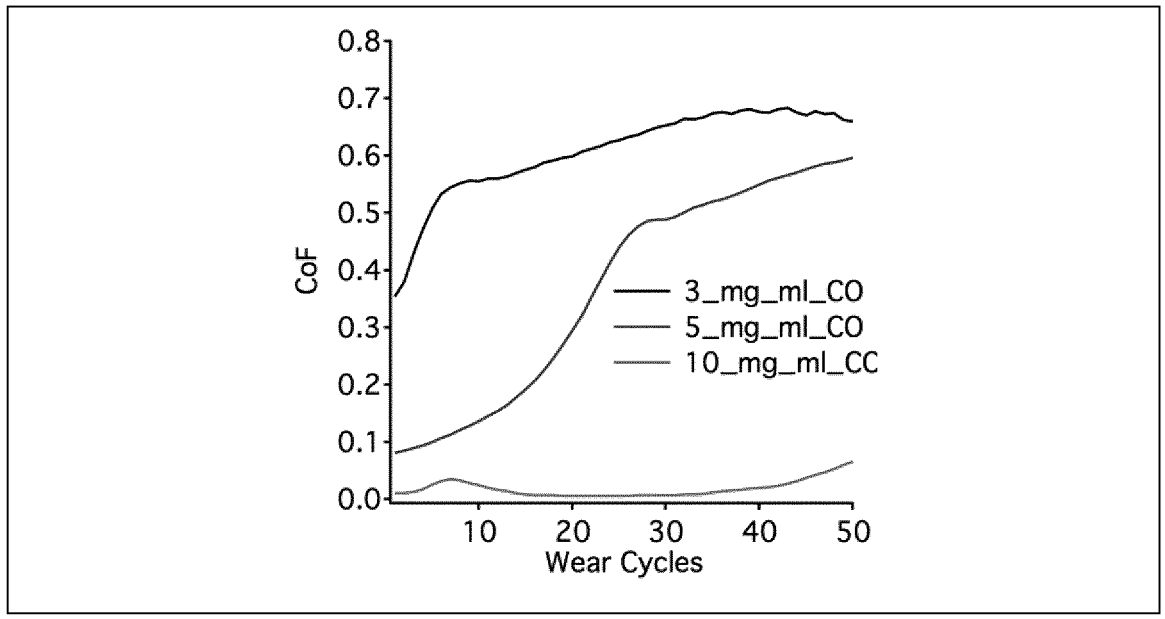
Figure 4: Coefficient of friction as a function of wear cycles (Normal Load : 1200 mN, PDMS pin countersurface).

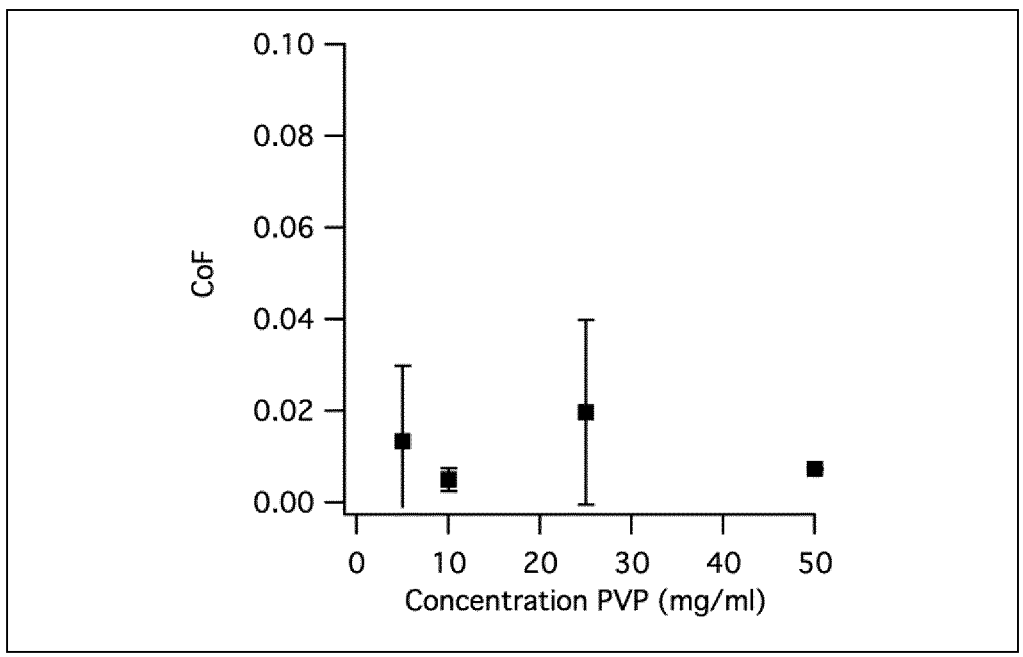
Figure 5: Coefficient of friction as a function of coating thickness as regulated through the absolute concentration of constituents in the coating formulation
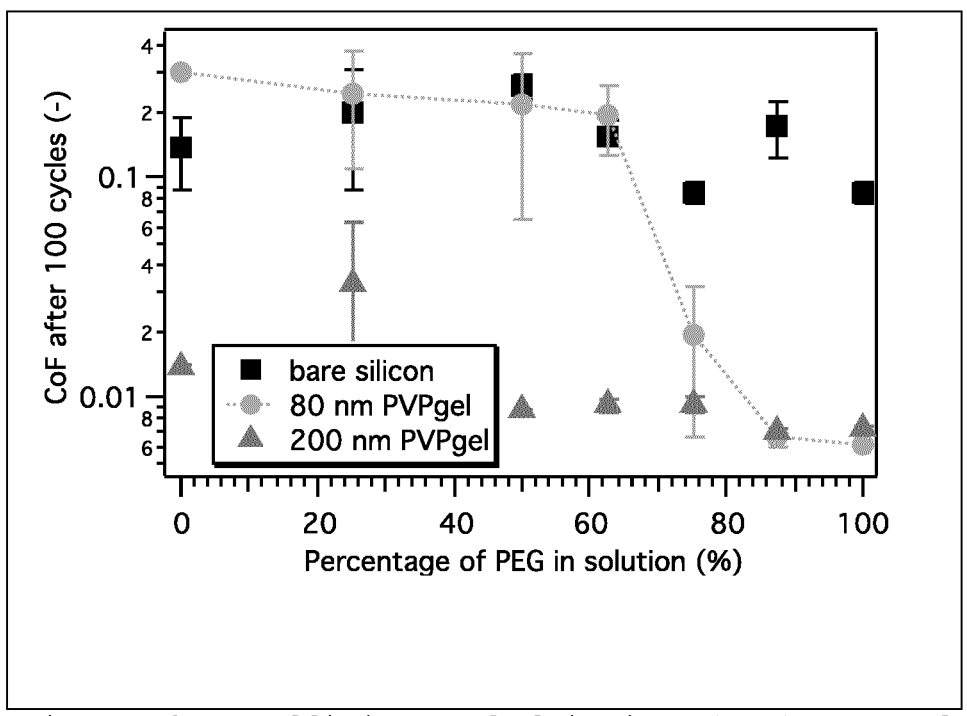
Figure 6: Coefficient of friction (CoF) as a function of percentage of PEG (400 g/mol) in water as viscosity modifier.

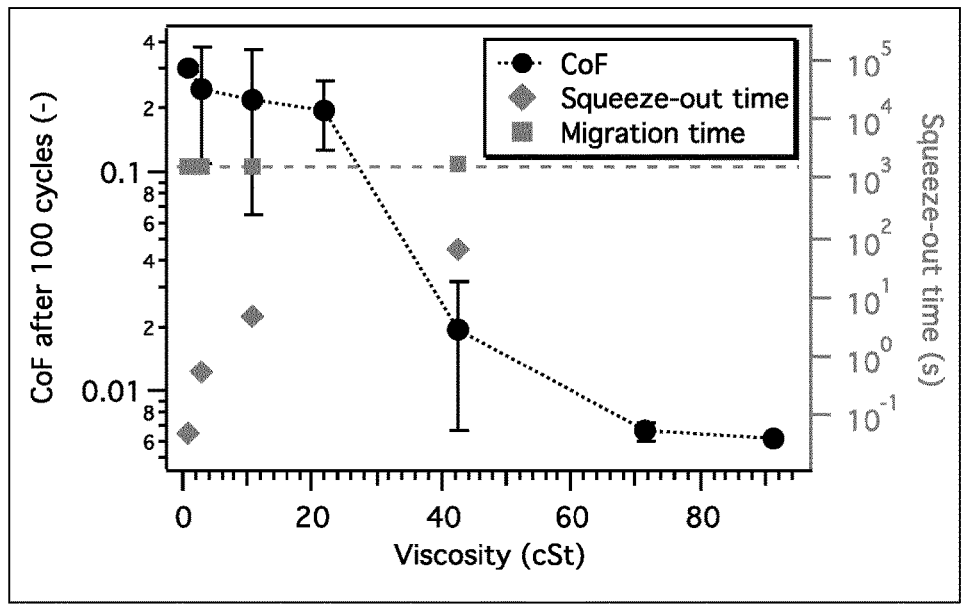
Figure 7: Coefficient of friction (CoF) after 100 cycles as a function of solution viscosity and calculated squeeze-out time.
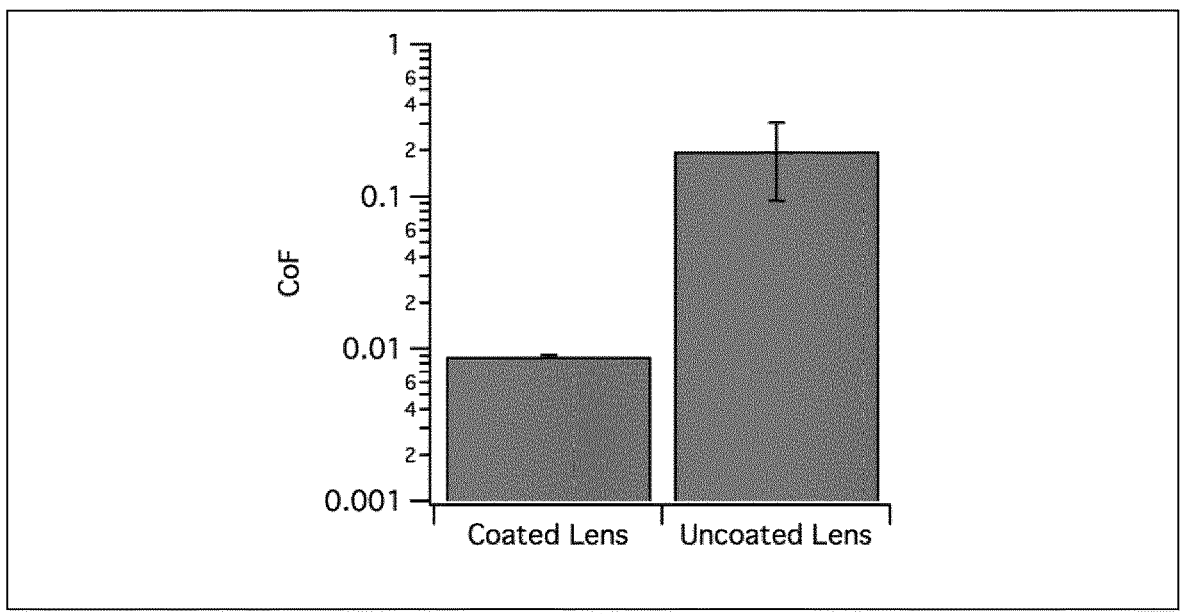
Figure 8: Coefficient of friction of coated (N=3) and uncoated (N=10) silicone-hydrogel lens.

DEVICE HAVING A SWITCHABLE WET-DRY LUBRICATING COATING

The present invention relates to a device having a switchable wet-dry lubricating coating.

Medical devices for insertion into a body cavity having a hydrophilic coating and providing a low friction surface, such as catheters, are known.

It has long been known that hydrophilic coatings with low friction are useful for a variety of medical devices. When low friction surfaces are used, the devices, upon introduction into the body, slide easily within arteries, veins, cannula and other body orifices and passageways. Thus, the discomfort experienced by the patient when the coated device is inserted into and removed from the body cavity is considerably reduced. The risk of damaging sensitive tissue in connection with the use of the device is at the same time considerably reduced.

There have been a wide variety of methods used to provide the desired surfaces. Typical known coatings having a low coefficient of friction and working either in wet conditions (hydrophilic coatings, brushes and hydrogels) or in dry conditions are e.g. Teflon®, silicone-based coatings and graphite. For example, EP 0 483 941 discloses a hydrophilic, lubricious, organic coating which comprises a polyvinylpyrrolidone and a crosslinked polyurethane resulting in a coating that works in wet conditions.

Hydrophilic coatings that have low coefficients of friction (CoF) are typically hydrogels and work because of confined water that forms a lubricating film upon rubbing against a counter surface. Once such coatings become dry, the CoF increases dramatically due to strong adhesive forces between contacting soft, hydrophilic surfaces leading to catastrophic failure of the coating.

In the case of coatings that lubricate in dry conditions, mainly polytetrafluoroethylene (PTFE) and silicone-based coatings, the lubricating mechanism is based on low adhesion between macromolecules that allow those molecules to easily slip along each other. A similar mechanism applies for layered materials such as graphite, hexagonal boron nitride or molybdenum disulfide where crystalline layers in the material can easily shear along each other.

When such coatings are immersed in water, typically the CoF increases due to hydrophobic-hydrophobic interactions and because water does not act as a lubricant even under shear due to its low viscosity. Especially super low CoF (that is below 0.01), like in the case of hydrogel coatings, are not achieved in wet conditions with the above-mentioned materials for dry lubrication.

A different way to obtain lubricated contacts is to use oils as lubricants that can separate contacts under shear due to their viscous properties.

Using a mixed model of dry and oil lubrication are so called "SLIPS" (slippery liquid infused porous surfaces) that have been disclosed in several documents. For example, WO 2014/012080 discloses a device, wherein the slippery surface covers an inner and/or outer surface. The slippery surface comprises either a lubricating layer or a liquid-polymer composite overlayer. SLIPS contain fluorosilicone or perfluorinated polymers which should be avoided for ecological reasons. WO 2014/209441 discloses a body which has a lubricant reservoir comprising a porous hydrophobic polymeric body and a lubricating liquid, said lubricating liquid is occupying the pores to provide a lubricated porous surface having a lubricant reservoir and a lubricant overlayer over the polymer surface. Also here, perfluorinated networks are used to produce the porous polymeric body. In addition, the lubrication of the surface is always provided by the lubrication agent comprised within the SLIP. That is, in wet and in dry condition, the lubricating agent of the surface is responsible for the lubrication effect.

WO 2006/037321 discloses a medical device which has a wetted hydrophilic coating comprising a coating composition containing a urethane-based hydrophilic polymer and a wetting agent comprising water and one or more lubricant(s). The coating is only linked by physical bonding, covalent attachments or crosslinks between the coating components do not exist. The coating of the medical device is carried out by injection moulding or by coextrusion requiring a specific equipment and therefore, increasing the costs. Moreover, such a coating has the disadvantage that there is no direct linkage to the surface of the device resulting in wrinkles which can cause cracks in the coating.

EP 2 236 524 discloses an adhesion promoter based on a functionalized macromolecule comprising photoreactive groups. Such adhesion initiators may be used, for example, for nail enhancements, such as cosmetic nail extensions, artificial fingernails, and/or nail modeling and repair systems.

The problem of the present invention is to provide a device having a lubricating coating which works in dry and/or in wet conditions and which can be produced both simply and at a low price.

The problem is solved by a device according to claim 1. Further preferred embodiments are subject of the dependent claims.

The device according to the present invention may be used in wet and/or in dry conditions. It comprises a lubricating coating, which is covalently bound directly on its surface or on an optional adhesion layer arranged on the surface of the device. The lubricating coating comprises at least one polymer A, at least one cross-linker, comprising a core and at least two reactive groups, and at least one lubricant.

A portion of the at least two reactive groups of the cross-linker are covalently linked to the polymer A to form a three-dimensional network in which the lubricant is incorporated and at the same time another portion of the reactive groups of the cross-linker are covalently linked to the surface of the device or to the optional adhesion layer on the surface of the device. That is, the cross-linker acts at the same time as cross-linking agent and as adhesion agent. A tight adhesion of the lubricating coating is particularly important in order not to lose the lubrication effect while moving the device, in particular, in the body of a patient.

The at least one polymer A is selected from the group consisting of polyvinylpyrrolidone (PVP), linear or branched polyethyleneglycol (PEG), dextran, polyalkyloxazolines (PAOXA), poly(2-methyl-2-oxazoline) (PMOXA), poly(ethyl-oxazoline) (PEOXA), hyaluronic acid, polyvinylalcohol (PVA), poly(2-hydroxyethyl methacrylate) (pHEMA), poly(l-vinylpyrrolidone-co-styrene), poly(l-vinylpyrrolidone)-graft-(1-triacontene), poly(l-vinylpyrrolidone-co-vinyl acetate), poly(ethylene-co-vinyl alcohol), poly(ethylene-co-vinyl-pyrrolidone), poly(maleic acid), poly(ethylene-co-maleic acid), polyacrylic acid, poly(acrylamide), poly[N-(2-hydroxypropyl) methacrylamide] (PHPMA), poly(N-isopropylacrylamide)(PNIPAM), poly[(organo)phosphazenes], chitosan and its derivatives, xantham gum, starch, pectin, algin, agarose, cellulose and its derivatives such as cellulose esters, cellulose ethers, hydroxypropylmethyl cellulose (HPMC) and hydroxyethyl cellulose (HEC) or a mixture thereof.

The at least one cross-linker comprises a core and at least two reactive groups, wherein the core is selected from the group consisting of polyallylamine (PAAm), polyethylene glycol (PEG), polyvinylpyrrolidone (PVP), polyethyleneimine (PEI), polylysine (PLL), polyacrylic acid (PAA), polyvinylalcohol (PVA), polyaspartic acid, dextran, chitin, chitosan, agarose, albumin, in particular bovine serum albumin (BSA), fibronectin, fibrinogen, keratin, collagen, lysozyme and multivalent molecules having less than 20 carbon atoms.

The reactive groups of the cross-linker are each independently selected from the group consisting of

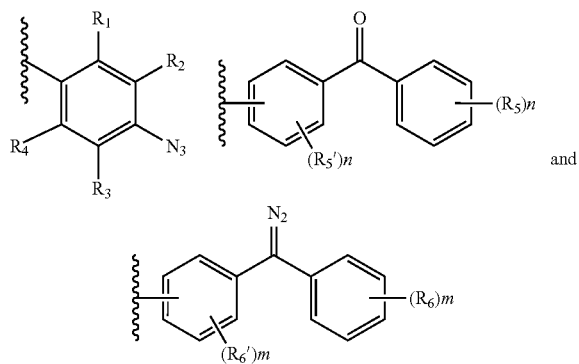

and and mixtures thereof, wherein $R_1$, $R_2$, $R_3$, and $R_4$ are, independently from one another, H, F or Cl; and $R_5$ and $R_5'$ is independently methyl, ethyl, propyl, isopropyl or dimethylamine and n is 0 to 4 and $R_6$ and $R_6'$ is independently methyl, ethyl, propyl, isopropyl or dimethylamine and m is 0 to 4 and the core is linked to the reactive group by a linker group B selected from the group consisting of a secondary or tertiary amine, an ether, a thioether, a carboxylic acid ester, an amide and a thioester.

The three-dimensional network formed by the polymer A and at least one the cross-linker is a matrix in which the at least one lubricant is incorporated, respectively confined. Either the matrix or the lubricant generates low friction because of their interaction in one specific medium against a surface. The lubricating coating of the present invention is a dual system working in wet and/or in dry conditions. When applying pressure, the lubricant is lubricating the surface of the device in dry conditions because the lubricant migrates to the surface of the coating and forms a film, that prevents the contact between the two sliding surfaces. In wet conditions, that is for example in water, water from the outer environment migrates into the three-dimensional network and forms a hydrogel. Under pressure, the water migrates to the surface of the hydrogel and forms a thin film, which is together with the hydrogel responsible for the lubricating effect. Due to the contact with the hydrogel, the water film is not directly mixed with the water of the outer environment.

Within the context of the invention, "lubricating" is defined as having a slippery surface. For example, a coating on the outer or inner surface of a medical device according to the present invention, is considered lubricious if it can be inserted into the intended body part without leading to injuries and/or causing unacceptable levels of discomfort to the patient. In particular, a coating is considered lubricated if the friction can be reduced compared to the friction measured in absence of the coating. Preferably, the coefficient of friction (COF) is less than 0.5 measured by a tribometer.

Within the context of the present invention, the term "wet" means "containing water", such as in water, in blood, in urine, in tears, saliva or other body fluids. In particular, the term is used herein to describe a coating that contains sufficient water to be lubricious. In terms of the water concentration, usually a wet coating contains at least 10 wt % of water, based on the dry weight of the coating, preferably at least 50 wt %, based on the dry weight of the coating.

Within the context of the present invention, the term "dry" means "in absence of water" and in particular "in contact with air", but encompasses also completely water free. Air may of course be humid. Typical examples for dry conditions are storage in a package, and the entrance of a body cavity before the device gets "wetted" by body fluids.

The three-dimensional network is permeable for the lubricant, thus allowing migration of the lubricant to the surface.

By combining a chemically bound three-dimensional network in form of the matrix with a non-chemically bound lubricant, but having at the same time a certain chemical affinity with said three-dimensional network, it is possible to form a substantially non-dripping film on the surface of the three-dimensional network. Since high viscosity liquid reduce wear, but increase friction and vice versa, it is an advantage to incorporate the lubricant in the matrix to have only a high viscosity fluid locally in the contacting area. Thus, the coating of the device according to the present invention performs better than using the lubricant alone.

In both wet and dry conditions, a lubricant coating is present. In dry conditions, the lubricant is inside and on the surface of the coating, and in wet conditions water from the outer environment migrates into the three-dimensional network, so that the network converts into a swelling matrix forming a hydrogel surface which is then together with the water responsible for the lubricating effect.

The combination of the pores and the viscoelastic properties of the three-dimensional network, that is mesh size, permeability, choice of polymer A, modulus and thickness as well as the viscosity of the lubricant, a low coefficient of friction can be obtained in both wet and dry conditions.

The at least one polymer A comprised in the lubricating coating of the present invention is selected from the group consisting of polyvinylpyrrolidone (PVP), linear or branched polyethyleneglycol (PEG), preferably linear polyethyleneglycol, dextran, polyalkyloxazolines (PAOXA), poly(2-methyl-2-oxazoline) (PMOXA), poly(ethyl-oxazoline) (PEOXA), hyaluronic acid, polyvinylalcohol (PVA), poly(2-hydroxyethyl methacrylate) (pHEMA), poly(l-vinylpyrrolidone-co-styrene), poly(l-vinylpyrrolidone)-graft-(1-triacontene), poly(l-vinylpyrrolidone-co-vinyl acetate), poly(ethylene-co-vinyl alcohol), poly(ethylene-co-vinylpyrrolidone), poly(maleic acid), poly(ethylene-co-maleic acid), polyacrylic acid, poly(acrylamide), poly[N-(2-hydroxypropyl) methacrylamide] (PHPMA), poly(N-isopropylacrylamide)(PNIPAM), poly[(organo)phosphazenes], chitosan and its derivatives, xantham gum, starch, pectin, algin, agarose, cellulose and its derivatives such as cellulose esters, cellulose ethers, hydroxypropylmethyl cellulose (HPMC) and hydroxyethyl cellulose (HEC) or a mixture thereof. The at least one polymer A has to be soluble in the liquid in which the coating is used in (in general water) and has preferably dangling chains that can form a brush-type surface in said liquid. The characteristics of the three-dimensional network can be modified by mixing two or more different types of polymer A. The hydrophilic nature of said polymer A allows a good lubrication effect in water due to the hydrogel formed by said polymer.

Generally, the at least one polymer A has a molecular weight in the range of 20,000 to 5,000,000 g/mol, preferably in the range of 50,000 to 3,000,000 g/mol and more preferably in the range of 200,000 to 2,000,000 g/mol.

The at least one cross-linker of the lubricating coating according to the present invention comprises a core and at least two reactive groups. The core is selected from the group consisting of polyallylamine (PAAm), polyethylene glycol (PEG), polyvinylpyrrolidone (PVP), polyethyleneimine (PEI), polylysine (PLL), polyacrylic acid (PAA), polyvinylalcohol (PVA), polyaspartic acid, dextran, chitin, chitosan, agarose, albumin, in particular bovine serum albumin (BSA), fibronectin, fibrinogen, keratin, collagen, lysozyme, and multivalent molecules having less than 20 carbon atoms. The at least one cross-linker has a significant influence on the characteristics of the matrix. By changing the ratio between polymer A and the amount of cross-linker, the pore size of the resulting three dimensional network can be tuned. High amounts of cross-linker lead to smaller pores and a stiffer gel than low amounts of cross-linker. Polymeric cores having preferably a molecular weight from 1,000 g/mol to 1,000,000 g/mol are preferred. If the core of the polymeric cross-linker is charged, the interaction of the matrix with oppositely charged molecules can be tuned. If the core of the polymeric cross-linker is uncharged, a neutral network is obtained.

The thickness of the lubricating coating, the crosslink-density of the three-dimensional network, the choices of both the polymer A and the cross-linker as well as the affinity between the three-dimensional network and the lubricant influence the local viscosity of the lubricating coating. Therefore, depending on the desired properties of the surface to be protected, the architecture of the three-dimensional network can be adapted.

Preferably, the core of the polymeric cross-linker comprises on average a functionalized side chain comprising the reactive group on at least every $24^{th}$, preferably on at least every $12^{th}$, more preferably on at least every $4^{th}$ repeating unit. In the case of a core comprising of a protein, the reactive group is typically attached to the side chain of the amino acid unit. The distribution of the side chains is usually statistical. Thanks to the multiple side chains comprising the reactive groups, it is possible to form a permanent covalent bonding between the cross-linker and the polymer A and the surface of the device as well as on the adhesion layer, if present.

Due to the fact that the reactive group is an integral part of the cross-linker comprised in the coating according to the present invention, it is possible to directly control the cross-linking rate of the three-dimensional network and the adhesion on the surface of the device and therefore to determine the physical properties of the network. In contrast thereto, free UV-initiators tend to a random polymerization, and therefore to the loss of control. In addition, no care needs to be taken about the presence of oxygen, which needs to be controlled (or completely avoided) in free radical polymerizations.

Preferably, the core of the at least one cross-linker is selected from the group consisting of polyallylamine (PAAm), polyvinylpyrrolidone (PVP), linear or branched polyethyleneimine (PEI), poly-D-lysine (PDL), poly-L-lysine (PLL) and epsilon poly-L-lysine (ε-PLL). PAAm, PVP, PEI, PDL, and ε-PLL are available in a wide variety of molecular weights. Useful PEI polymers range in molecular weight from 1,000 g/mol to 1,000,000 g/mol.

In another embodiment, the core of the at least one cross-linker is a multivalent molecule having less than 20 carbon atoms. Examples of such core molecules are molecules with 2 to 6 ethylene oxide units, sugar such as monosaccharides and disaccharides, multifunctional alcohols such as ethylene glycol, trimethylolpropane, glycerine, oligoglycerine, pentaerythritol, tris(2-aminoethylamine), N,N,N',N'-tetrakis(3-aminopropyl)-1,4-butanediamine, 2,2'-(ethylenedioxy)bis(ethylamine), 1,2,3-propanetricarboxylic acid, 2-hydroxy propane-1,2,3-tricarboxylate, 1-hydroxy propane-1,2,3-tricarboxylate, tri(carboxymethyl)amine and diethylaminetriamine.

The reactive groups of the cross-linker are each independently selected from the group consisting of

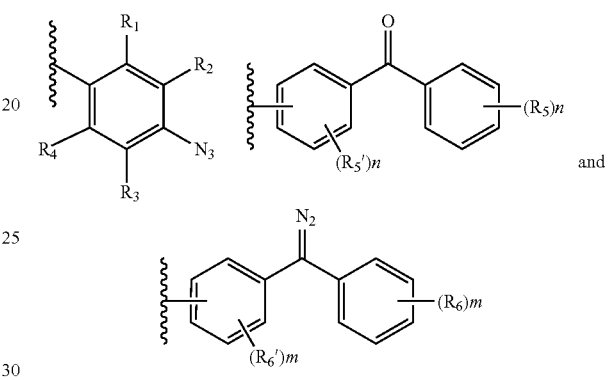

and mixtures thereof, wherein $R_1$, $R_2$, $R_3$ and $R_4$ are, independently from one another, H, F or Cl; and $R_5$ and $R_5'$ is independently methyl, ethyl, propyl, isopropyl or dimethylamine and n is 0 to 4, and $R_6$ and $R_6'$ is independently methyl, ethyl, propyl, isopropyl or dimethylamine and m is 0 to 4, and the core is linked to the reactive group by a linker group B selected from the group consisting of a secondary or tertiary amine, an ether, a thioether, a carboxylic acid ester, an amide and a thioester.

Preferably, the at least two reactive groups of the cross-linker are all the same.

Preferably, the reactive groups are selected from the group consisting of ortho, meta or para substituted benzophenones, diaryldiazomethanes, in particular diphenyldiazomethan and bis-4,4'-N,N-dimethylamino diphenyldiazomethane, phenylazide, optionally comprising one or more halogen substituents in the ortho and meta positions and mixtures thereof, and perfluorophenyl azide (PFPA). PFPA is especially preferred. It is stable at ambient light and atmosphere and in basic and acidic conditions. The number of formed crosslinks by nitrene insertion compared to non-productive hydrogen abstraction is higher compared to phenylazide and benzophenone chemistry.

The photoreactive group, and in particular PFPA, allows for a fast and very efficient curing of the cross-linker by UV irradiation, preferably with a wavelength of less than 400 nm, or by heat, preferably at a temperature of at least 120° C. Upon activation, the azide group is converted to a nitrene, which undergoes a very fast, non-specific insertion reaction into a nearby C—X bond of the surface of the device, the polymer A or the adhesion layer, if present.

The coating of the device according to the present invention comprises at least one lubricant, which is a substance that forms a fluid phase inside the three-dimensional network. Preferably, the lubricant is selected from the group consisting of an edible oil, a fat from plants, a fat from animals, a lipid and a hyaluronate or a mixture thereof. Especially preferred are castor oil, hydrogenated castor oil, or soy bean oil, in particular in medical application.

Alternatively, the lubricant may be a synthetic oil, preferably selected from the group consisting of poly-alpha-olefine (PAO), polyethyleneglycole, a silicone oil such as silicon oil having a viscosity of 1000 cst at 25° C. or silicone oil having a viscosity of 10000 cst at 25° C. and silicone paste such as Si HS—N from momentive (Si HS—N).

Most preferably the lubricant is selected from the group consisting of polyethylene glycol (PEG) with a melting point below 20° C., polyethylene glycol (PEG) with a melting point between 20° C. and 50° C., polyethylene gylcol (PEG) with a melting point above 50° C., glycerin, glyceryl trioleate, mineral oils, polyolefins including poly-alpha-olefins (PAO), white mineral oil, synthetic esters, such as polyol esters, polyalkyleneglycols (PAG), phosphate esters, liquid or oily silicones, ionic liquids, liquid graphite, plant wax, animal wax, petroleum derived wax, mineral wax, release agents used in injection molding such as lecithin, viscosity enhancing agents such as poloxamer (Pluronic®), polyacrylate gels, methylcellulose, lubricant from above list mixed with a viscosity enhancer, vegetable oils and fats and animal oils and fats.

Possible vegetable oils and fats are listed as follows: oil of soybeans, oil of groundnuts, oil of coconuts, oil of palm, oil of palm kernel, oil of virgin olives, oil of olives residues, butter of Shea nuts, oil of castor beans, castor oil hydrogenated, oil of sunflower seed, oil of rapeseed, canola oil, oil of tung nuts, jojoba oil, oil of safflower seed, oil of sesame seed, oil of mustard seed, oil of poppy seed, vegetable tallow, oil of kapok, stillingia oil, oil of cottonseed, oil of linseed, oil of hempseed, oil from *Borago officinalis* seeds, oil of vegetable origin nes, oil of rice bran, terpenoid esters such as linalyl acetate and oil of maize.

Possible animal oils and fats are listed as follows:

Fat of cattle, butcher fat, fat of buffalo, fat of sheep, fat of goats, fat of pigs, lard, fat of poultry, fat of camels, fat of other camelids, animal oils and fats obtained from other animal species, oils and fats recovered from guts, feet, sweepings and hide trimmings, lard stearin and lard oils, tallow, liquid margarine, margarine, shortening (product similar to margarine, but with a higher animal fat content), fat preparations, boiled oils, dehydrated oils, hydrogenated oils and fats, wool grease and lanolin, degras, fatty acids, fatty acid esters, such as oleic acid propyl ester and methyl 10-undecenoate, spermaceti, oil from fish and marine mammals.

Possible lipids are for examples cholesterol and cholesteryl derivatives such as cholesteryl linoleate.

The choice of the lubricant depends on the desired surface properties and on the application of the device. In the medical field the toxicity of the lubricant is important. In order to avoid a two-phase system, polymer A and the lubricant are preferably miscible. Preferred are oils and fats that do not lead to a dripping, greasy surface but still provide the desired slipperiness.

Oils derived from the seeds of *Borago officinalis* are especially preferred for coatings of medical devices in the gastrointestinal, respiratory and cardiovascular field such as catheters since they have additionally an anti-inflammatory effect because of their high content of γ-linolenic acid.

The lubricant can act as a viscosity modifier by itself, or an additional viscosity modifier can be added to the liquid in the wet state to improve wear resistance. Preferably, the coating does not comprise an additional viscosity modifier.

In order to increase the adherence between the surface of the device and the three-dimensional network, an optional adhesion layer may be present.

Preferably, the adhesion layer comprises or consists of the same cross-linker as described above. That is, the adhesion layer is formed by an adhesion layer composition comprising or consisting of the same cross-linker which is used for the formation of the three-dimensional network. Due to the same products being used, a coated device such as a medical device is cheaper and reduces the effort to comply with the regulatory requirements.

The device according to the present invention is preferably a medical device. The coating can be coated on a device which may be selected from a range of geometries and materials. The device may have a texture, such as porous, non-porous, smooth, rough, even or uneven. The device supports the lubricating coating directly on its surface or on an adhesion layer on its surface. The surface may be untreated or treated in order to facilitate the coating of the surface or in order to sterilize the device before the coating. The coating can be on all areas of the device or on selected areas. It can be applied to a variety of physical forms, including films, sheets, rods, tubes, molded parts (regular or irregular shape), fibers and fabrics. Examples of suitable surfaces to be coated are for instance surfaces that consist of or comprise metals, plastics, ceramics, glass and/or composites.

The device is preferably a medical device, such as injection needles, cannulas, syringe pistons, membranes, catheters such as urinary catheters and respiratory catheters, blades, surgical instruments, in particular sharp tools, single use razor-blades, insertion devices, guide wires, and in particular cardiovascular guide wires, stents, a stent graft, contact lenses and intraocular lens (IOL) injection devices, cochlear implants, anastomotic connectors, synthetic patches, electrodes, sensors, angioplasty balloons, wound drains, shunts, tubing, infusion sleeves, urethral inserts, pellets, implants, blood oxygenators, pumps, vascular grafts, vascular access ports, heart valves, annuloplasty rings, sutures, surgical clips, surgical staples, pacemakers, implantable defibrillators, neurostimulators, orthopedic devices, cerebrospinal fluid shunts, implantable drug pumps, spinal cages, artificial discs, replacement devices for nucleus pulposus, ear tubes, intraocular lens and any tubing used in minimally invasive surgeries. Most preferably, the medical device is selected from the group consisting of injection needles, cannulas, syringe pistons, membranes, catheters, blades, surgical instruments, in particular sharp tools, single use razor-blades, insertion devices, guide wires, stents, a stent graft, contact lenses and IOL injection devices and cochlear implants.

The coating of the device according to the present invention may comprise at least two different cross-linkers. Preferably, the at least two different cross-linkers have a different core. This allows to produce a three-dimensional network having locally different lubrication characteristics. Alternatively, or in addition, the grafting ratio may be adjusted by varying the ratio of the polymeric core of the cross-linker to reactive group to tune the distance between crosslinking positions. Grafting ratios between 4 and 100 can be easily prepared. Preferably, the one of the at least two different crosslinkers is uncharged and the other one is charged. For example, the at least two different cross-linkers may be polyethyleneimine-grafted-perfluorophenylazide (PEI-g-PFPA) and 2,2'-(ethylenedioxy)bis(ethylamine-PFPA).

Especially good results can be obtained with coatings wherein the cross-linker is selected from the group consisting of polyethyleneimine-grafted-perfluorophenylazide (PEI-g-PFPA), tris(2-PFPA-aminoethyl)amine and 2,2'-(ethylenedioxy)bis(ethylamine-PFPA). Charged cross-linkers such as PEI-g-PFPA have the advantage that they are protonated in water. Uncharged cross-linkers such as 2,2'-(ethylenedioxy)bis(ethylamine-PFPA) have the advantage that they do not bind negatively charged biomolecules which sometimes has to be avoided.

The polymer A may be used in more than 10 wt %, for example more than 15 wt % or more than 50 wt %, based on the total weight of the dry coating. The polymer A can be present up to 95%, based on the total weight of the dry coating. Preferably, the ratio between the polymer A and the cross-linker is between 100:1 and 2:1 by weight, preferably 50:1 and 2:1 by weight, most preferably 5:1 and 2:1.

The ratio between the three-dimensional network and the lubricant is preferably between 20:1 and 1:2 by weight, most preferably between 10:1 and 1:1 by weight, and in particular preferably between 2:1 and 1:1 by weight.

Preferably, the coating contains no additional UV-radical-initiators such as AIBN, trichloroacetophenone or benzoin isopropyl ether. Since no UV-radical-initiators are used during production, the coating is free from UV-radical-initiators and therefore allows a long-term stability of the coating.

The invention further relates to a method of forming a device comprising a lubricating coating in dry and in wet conditions.

Preferably, the device according to the present invention is prepared by
 a. preparing a coating formulation comprising the at least one polymer A, the at least one cross-linker and at least one solvent,
 b. applying the coating on the surface of the device or on its optional adhesion layer,
 c. forming a three-dimensional network and simultaneously linking the network to the surface of the device or to its optional adhesion layer by radiation or/and by heat, wherein the lubricant is added to the coating formulation or
 after the formation of the three-dimensional network.

The at least one solvent is preferably a standard solvent in which the at least one polymer A and the at least one cross-linker are soluble. Instead of one single solvent also solvent mixtures may be used.

Due to the fact, that the three-dimensional network and the covalent bonding of the cross-linker to the surface of the device or to the optional adhesion layer is carried out at the same time, that is, in one single step, the method according to the present invention is extremely fast and cost-efficient. The linkage to the surface of the device is very stable. Since the cross-linker is responsible for the three-dimensional network and for the linkage to the surface of the device, the coating is free of cracks.

The lubricant can be incorporated into the three-dimensional network by adding the lubricant directly into the coating formulation in one step or sequentially by loading the formed three-dimensional network with said lubricant. The one-step method has the advantage that a uniform distribution of the lubricant can be obtained and that the method is faster and therefore, less expensive.

Alternatively, the lubricant can be added to the final three-dimensional network, that is, after curing. This method allows to have different types of lubricants on the same device which may be necessary depending on its use.

The coating formulation can be applied to the device by jetting, spraying, dip-coating, printing, painting, filling and emptying, washing, rolling and other methods known in the art.

The thickness of the coating may be controlled by the soaking time, drawing speed or viscosity of the coating formulation. Typically, the thickness of a coating on a substrate ranges from 0.05-300 µm, preferably 0.05-100 µm, more preferably 0.1-30 µm.

Preferably, the coating of the device according to the present invention further comprises a fluorescent marker. The fluorescent marker allows to determine where the coating has been applied. Most preferably, the fluorescent marker is polyethyleneimine-grafted-salicylic acid (PEI-g-salicylate, since it additionally stabilizes the coating formulation.

The coating of the device according to the present invention may comprise additional additives or the lubricant itself can have other benefits such as acting as a drug, UV-stabilizer, anti-oxidant, plasticizer, antistatic agent, porogen, pigment, whitener or a dye.

In addition, oil-soluble drugs or vitamins may be added to the lubricant and therefore be incorporated into the three-dimensional network.

The accompanying drawings illustrate embodiments of the devices according to the present invention, explain some results together with the description and serve to explain the principles of the present disclosure.

FIG. 1a and FIG. 1b show a schematic view of the present invention.

Figure 2:
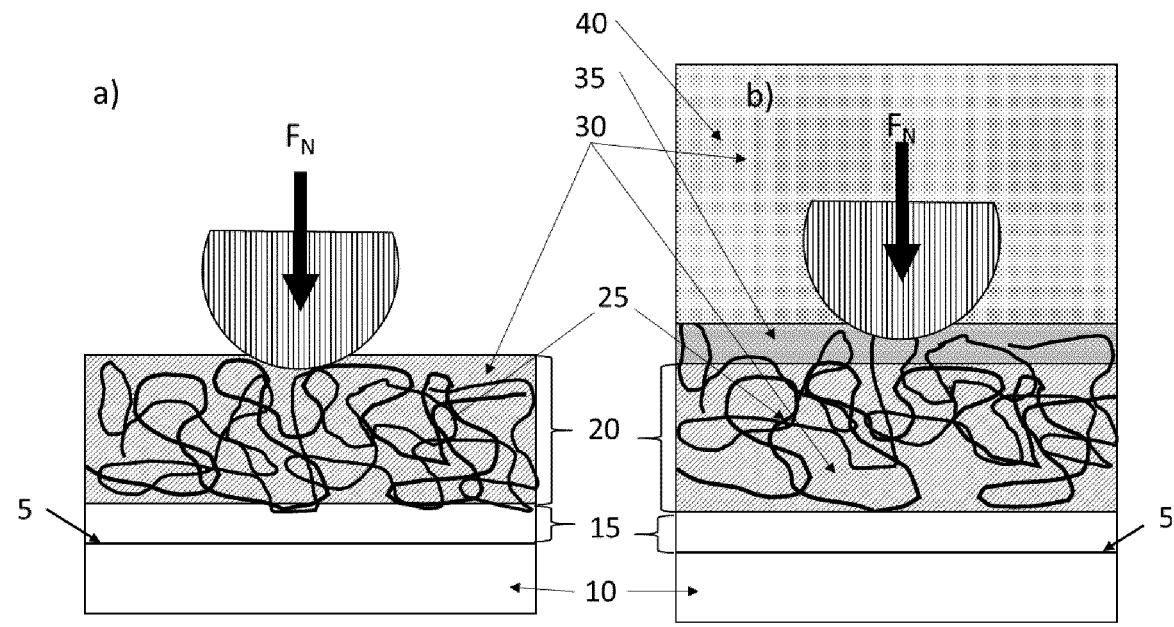

FIG. 2a and FIG. 2b show a schematic view of another embodiment of the present invention FIG. 3 shows the coefficient of friction as a function of castor oil concentration in the coating formulation FIG. 4 shows the coefficient of friction as a function of wear cycles FIG. 5 shows the coefficient of friction as a function of coating thickness FIG. 6 shows the coefficient of friction as a function of percentage of PEG in water as viscosity modifier.

FIG. 7 shows the coefficient of friction after 100 cycles as a function of solution viscosity FIG. 8 shows the coefficient of friction of coated and uncoated silicone-hydrogel lens.

FIGS. 1a and 1b show a schematic view of the present invention. On the surface (5) of the device (10) is an optional adhesion layer (15). On said optional adhesion layer is a coating (20) which comprises at least a polymer A, at least one cross-linker and a lubricant (30). The polymer A and the cross-linker form a three-dimensional network (25) which is covalently attached to the optional adhesion layer (15) of the device or directly to the device surface. The lubricant (30) is incorporated in the three-dimensional network (25). In dry, ambient conditions the lubricant is incorporated in the three-dimensional network and forms under pressure a lubricating film on the surface of the coating (FIG. 1a). In wet condition, that is in water, water from the outer environment migrates into the three-dimensional network and forms a hydrogel surface (35). Under pressure, the water migrates to the surface of the hydrogel and forms a thin film which is responsible for the lubricating effect. Due to the confinement of the water in the hydrogel (35) it is not directly mixed with the water of the outer environment (40) (FIG. 1b).

FIGS. 2a and 2b show a schematic view of further embodiment of the present invention. On the surface (5) of the device (10) is an optional adhesion layer (15). On said optional adhesion layer is a coating (20) which comprises at least a polymer A, at least one cross-linker. The polymer A and the cross-linker form a three-dimensional network (25) which is covalently attached to the optional adhesion layer (15) of the device or directly to the device surface. In wet condition, that is in water (40) which additionally comprises the lubricant (30), water and the lubricant from the outer environment migrate into the three-dimensional network and form a lubricant-hydrogel surface (35). Under pressure, the water and the lubricant migrate to the surface of the hydrogel and form a thin film which is responsible for the lubricating effect (FIG. 2*b*). In dry, ambient conditions the lubricant stays incorporated in the three-dimensional network and forms under pressure a lubricating film on the surface of the coating (FIG. 2*a*).

EXAMPLES

Example 1: Preparation of a Polyethyleneimine-Grafted-Perfluorophenylazide (PEI-g-PFPA) Stock Solution for Use as a Macromolecular Cross-Linker

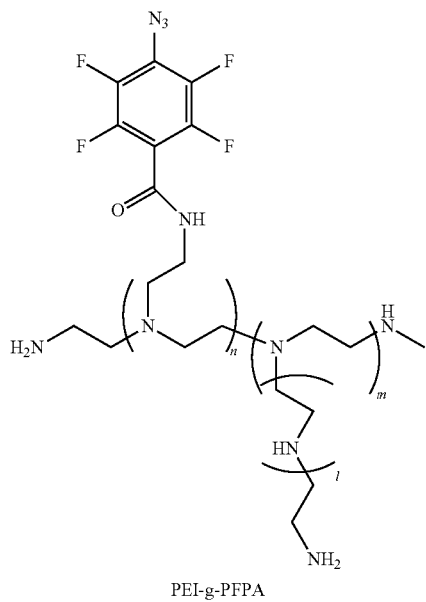

PEI-g-PFPA

A solution of branched polyethyleneimine (PEI, for example Aldrich 408727 average Mw 25,000 g/mol) in ethanol with a concentration of 100 mg/mL is prepared. 16.3 mL of this solution are placed inside a brown glass bottle with a magnetic stir bar. 2.09 g of perfluorophenylazide-N-hydroxy-succinimide (PFPA-NHS) are dissolved in a second bottle in 283.7 mL of ethanol. This PFPA-NHS solution is slowly added to the vigorously stirred PEI solution and stirred for more than 5 h at room temperature to obtain a PEI-g-PFPA stock solution with a nominal grafting ratio of ethyleneimine monomers to PFPA of 6 and a concentration of mg/mL. The grafting ratio of this polymer can be adjusted by varying the ratio of PEI to PFPA to tune the distance between crosslinking positions. Grafting ratios between 4 and 100 can be easily prepared. Higher concentrations are possible by reducing the amount of solvent in the synthesis or by evaporation.

Example 2: Preparation of a Polyethyleneimine-Grafted-Salicylic Acid (PEI-g-Salicylate) Stock Solution as Radical Quencher (Stabilizer) and Fluorescent Marker

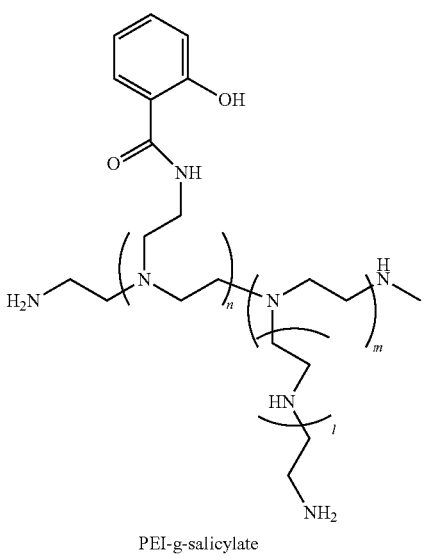

PEI-g-salicylate

A solution of branched polyethyleneimine (PEI, for example Aldrich 408727 average Mw 25,000 g/mol) in ethanol with a concentration of 100 mg/mL is prepared. 7.57 mL of this solution are placed inside a brown glass bottle with a magnetic stir bar. 0.413 g of salicylate-N-hydroxy-succinimide (salicylate-NHS) are dissolved in a second bottle in 92.4 mL of ethanol. This salicylate-NHS solution is slowly added to the vigorously stirred PEI solution and stirred for more than 5 h at room temperature to obtain a PEI-g-salicylate stock solution with a nominal grafting ratio of ethyleneimine monomers to salicylate of 10 and a concentration of 10 mg/mL. The grafting ratio of this polymer can be adjusted by varying the ratio of PEI to salicylic acid to tune the distance between fluorophore positions. Grafting ratios between 4 and 100 can be easily prepared. This polymer is fluorescent with an emission wavelength of 400 nm. Salicylic acid also has a high reaction rate with hydroxyl free radicals and acts therefore as stabilizer for the coating formulation.

Example 3: Preparation of a Tris(2-PFPA-Aminoethyl)Amine as Cross Linker

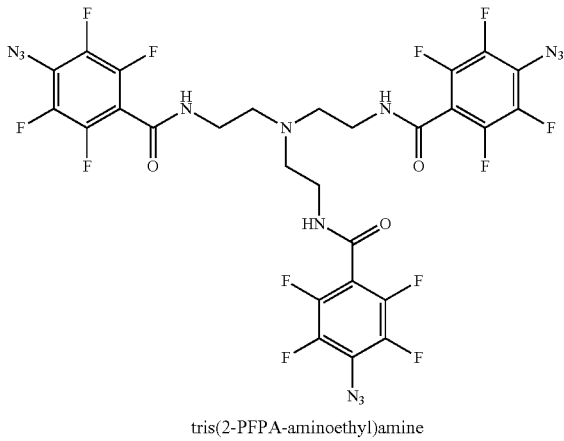 [SMILES: [N-]=[N+]=Nc1c(F)c(F)c(C(=O)NCCN(CCNC(=O)c2c(F)c(F)c(N=[N+]=[N-])c(F)c2F)CCNC(=O)c2c(F)c(F)c(N=[N+]=[N-])c(F)c2F)c(F)c1F]

tris(2-PFPA-aminoethyl)amine

Tris(2-aminoethyl)amine is dissolved in dichloromethane and 3.1 eq of perfluorophenylazide-N-hydroxy-succinimide (PFPA-NHS) are added to this solution. The mixture is stirred for 24 h. The product precipitates as a white powder that is filtered, washed with a small amount of cold dichloromethane and dried.

Example 4: Preparation of a 2,2'-(ethylenedioxy)bis(ethylamine-PFPA) Solution as Small Uncharged Cross-Linker

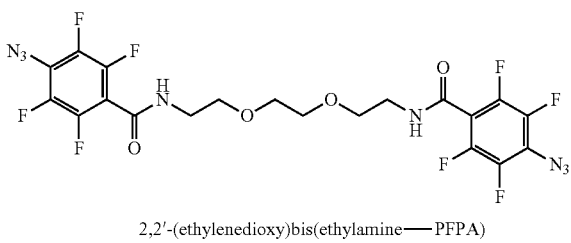

2,2'-(ethylenedioxy)bis(ethylamine—PFPA)

2.5 mL of 2,2'-(ethylenedioxy)bis(ethylamine) (10 mg/mL in ethanol, 0.171 mmol) and 113.8 mg perfluorophenylazide-N-hydroxy-succinimide (PFPA-NHS) are stirred overnight and diluted with 17.4 mL of ethanol to obtain a solution of 2,2'-(ethylenedioxy)bis(ethylamine-PFPA) which is used without further purification.

Example 5: Production of Coating Formulations Containing a Lubricant, PVP Matrix and PEI-g-PFPA as Cross-Linker A solution of high molecular weight polyvinylpyrrolidone (PVP K94, Aldrich 437190) in ethanol, ethylacetate (or any other solvent where PVP is soluble) is prepared. This solution can be mixed with different amounts of PEI-g-PFPA (10 mg/mL) (Example 1) as cross-linker, a lubricant containing solution and ethanol, ethylacetate (or any other solvent where PVP and the other components are soluble) to obtain coating formulations that have different viscosities depending on total concentration and lead to different cross-link densities and various amounts of confined lubricant after curing of the applied coating.

The following lubricants were tested:
Soy bean oil (Soy bean)
silicone oil (Si 1000 cst)
silicone oil (Si 10000 cst)
silicone paste (Si HS—N) from momentive (Si HS—N)
poly-alpha-olefin (PAO)
Castor oil (CO)

TABLE 1

Examples of solutions prepared as described in Example 5.

| Solution | OIL | TopCoat | TopCoat Solvent | Solvent Ethanol Percentage (wt %) |
|---|---|---|---|---|
| A | SOY BEAN | 25 mg/ml PVP, PVP: OIL = 0.6, PVP: HVE = 5 | EA | 62.5 |
| B | Si 1000 cst | 15 mg/ml PVP, PVP: OIL = 0.6, PVP: HVE = 5 | EA | 37.5 |
| C | Si 10000 cst | 12.5 mg/ml PVP, PVP: OIL = 0.6, PVP: HVE = 5 | EA | 31.25 |
| D | Si HS—N | 9.375 mg/ml PVP, PVP: OIL = 0.6, PVP: HVE 5 | EA | 23.4375 |
| E | PAO | 25 mg/ml PVP, PVP: OIL = 0.6, PVP: HVE = 5 | EA | 62.5 |
| F | CO | 25 mg/ml PVP, PVP: OIL = 0.6, PVP: HVE = 5 | Ethanol | 100 |

(Abbreviations EA: ethylacetate; HVE: PEI-g-PFPA; PVP: polyvinylpyrrolidone)

Example 6: Coating of Injection Needles

Stainless steel, hypodermic needles (G19, 1-½") were cleaned by oxygen plasma and coated with HVE primer as applied by spray coating from a 1 mg/ml in ethanol solution to form an adhesion layer. Coating solutions as described in Example 5 A-F were applied by spray coating on top of the primer layer. Coatings were cured by exposure to deep UV radiation (3-4 mW/cm$^2$ flux at 254 nm) for 15 min.

Example 7: Friction Testing of Coated Injection Needles in Wet and Dry Conditions The frictional properties of the coated needles in Example 6 were tested by means of micro tribometry (BASALT MUST, Tetra) and penetration through a skin mimic polyurethane (PU) foil (DEKA PU 0.4 mm thick). For tribometry testing, the needles were mounted in a 3D printed sample holder and fixed with a luer lock. A cylindrical counter surface made from poly dimethyl siloxane (elastic modulus ~2 MPa) was slid against the needle in a cross cylinder configuration at different normal loads between 400-1400 mN to extract the coefficient of friction (slope of frictional to normal forces). Additionally, to extract the wear resistance of the coating, the PDMS pin was slid back and forth over the needle at ~1200 mN normal load for 50 cycles while recording the frictional force. The experiment was conducted in the following sequence:
1. Coefficient of friction determination in the dry state
2. Wear resistance in the dry state
3. Wear resistance in the dry state for 10-20 cycles after which phosphate buffered saline was added to the sample holder to record the transition in friction when going from dry to wet state.

4. Coefficient of friction determination in the wet state.

Coefficient of friction wet and dry for the different coatings are measured. An uncoated needle was also measured, which had high friction and high adhesion to the counter surface. All coatings, except PAO, had reduced friction dry compared with the uncoated needle. All coatings had low CoF when immersed in PBS.

The frictional properties were further evaluated by measuring the force necessary to penetrate, and maintain motion through, a PU DEKA foil. The needle was mounted on a fixed force gauge (PCE-LFG 20, PCE instruments), and the PU foil suspended on a linear motion drive moving at 1 mm/s. The force was recorded both during insertion and withdrawal of the needle. The penetration phase was conducted dry, and during the withdrawal, the needle was wetted. An uncoated needle was measured and compared to coated ones. All coatings reduced the friction force dry compared to the uncoated needle, and castor oil, soybean oil and PAO had low forces in the wetted stage.

Example 8 Determining the Lubricant Capacity of PVP/PEI-g-PFPA Coatings

The solutions 1-6 (see Table 2) with increasing amounts of castor oil as lubricant content were prepared.

TABLE 2

Examples of different coating formulations prepared as described in Example 5.

| solution no. | conc. of PEI-g-PFPA [mg/mL] | conc. of PVP [mg/mL] | conc. of lubricant [mg/mL] | PVP to PEI-g-PFPA m/m ratio | castor oil to PVP ratio |
|---|---|---|---|---|---|
| 1 | 0.5 | 25 | 0 | 50 | 0 |
| 2 | 0.5 | 25 | 12.5 | 50 | 0.5 |
| 3 | 0.5 | 25 | 25 | 50 | 1 |
| 4 | 0.5 | 25 | 50 | 50 | 2 |
| 5 | 0.5 | 25 | 75 | 50 | 3 |
| 6 | 0.5 | 25 | 100 | 50 | 4 |

These solutions were spin-coated onto glass slides and cured for 2 min with UV-C (254 nm, 3.5 mW/cm$^2$). A clean aluminium foil is placed on the coating and slowly peeled off. Coatings with a ratio of castor oil to PVP below 2 (solutions 1-4) did not leave visible oil traces on the foil, while coatings with higher castor oil content left oil residues on the aluminium foil (solutions 5-6). A coating which does not leave oil traces on touching surfaces is preferred.

Example 9: Single Use Razor-Blade Plastic Casing

Razor blade casings were plasma cleaned for 2 min, and coated according to any of the three coating strategies outlined in Table 3. Primer solution I: 0.1 mg/ml PEI-g-PFPA in ethanol and II: 5 mg/ml PEI-g-PFPA in ethanol. After coating with primer solution II, the primer was cured for 4 min at 3.7 mW/cm$^2$ UV flux at 254 nm. Topcoat was applied by spray coating. After drying, the coating was cured for 5 min at 3.7 mW/cm$^2$ UV flux at 254 nm.

The tactile feeling of Coating No. 3 when dry was smooth and lubricious without being oily or greasy. All coatings were lubricious when immersed in water.

TABLE 3

Coating formulations and strategies for razor blade casings.

| | Adhesion layer | | | Lubrication coating | | | |
|---|---|---|---|---|---|---|---|
| Coating no. | Adhesion layer | UV curing after primer (Y/N) | conc. of PEI-g-PFPA [mg/mL] | conc. of PVP [mg/mL] | conc. of lubricant [mg/mL] | PVP to PEI-g-PFPA m/m ratio | castor oil to PVP ratio |
| 1 | I | N | 1 | 10 | 0 | 10 | 0 |
| 2 | II | Y | 1 | 10 | 0 | 10 | 0 |
| 3 | I | N | 2 | 10 | 6 | 5 | 0.6 |

Example 10: Coating of Pen Needles by Dip-Coating

Uncoated stainless steel pen needles (clickfine 31G×5/16", 0.25×8 mm) are used for the coating experiments. The needles are coated according the following procedure:
1. 2 minutes' oxygen plasma
2. Dip in PEI-g-PFPA (0.1 mg/mL in ethanol) solution for 10 sec to form an adhesion promoting layer
3. Dip in coating formulation according Table 4 for 10 sec
4. Dry in air
5. UV-C illuminate for 2 minutes in case of PVP coatings

TABLE 4

Examples of coating formulations used for pen needle coatings.

| Coating no. | description | Matrix | matrix crosslinking chemistry | lubricant | Matrix to lubricant ratio |
|---|---|---|---|---|---|
| 1 | PVP only | PVP | PEI-g-PFPA | none | — |
| 2 | HVE only | none | none | none | — |
| 3 | castor oil only | none | none | castor oil | — |
| 4 | PVP + 50% castor oil | PVP | PEI-g-PFPA | castor oil | 2:1 |

Example 11: Injection Force Measurements of Coated Pen Needles

Injection force was measured by injection of the needle into a 0.40 mm PU test foil while measuring the force with a Zwick Z2.5 force gauge. The results for the different coated needles are listed in Table 5 and compared to a standard siliconized Clickfine reference. Only for the coating where the matrix is combined with the lubricant castor oil (5) low values as for a siliconized reference needle can be obtained for dry friction. PVP only or PHEMA only as well as cross-linker only or castor oil only leads to higher friction values. PVP containing castor oil based coatings resist gamma sterilisation.

TABLE 5

Maximal injection force (Fmax) and average friction force (Fmid) for different coated clickfine pen needles.

| Coating no. | Coating | Fmax Injection (N) | Fmid Friction (N) |
|---|---|---|---|
| — | Clickfine (Reference siliconized) | 0.52 ± 0.08 | 0.27 ± 0.07 |
| 1 | PVP only | 1.55 ± 0.13 | 1.39 ± 0.10 |
| 2 | PHEMA only | 1.48 ± 0.10 | 1.25 ± 0.05 |
| 3 | HVE only | 1.02 ± 0.06 | 0.59 ± 0.071 |
| 4 | Castor oil only | 0.85 ± 0.03 | 0.24 ± 0.04 |
| 5 | PVP + 50% castor oil, HVE | 0.68 ± 0.06 | 0.22 ± 0.03 |
| 5 | PVP + 50% castor oil, HVE - gamma sterilized | 0.77 ± 0.06 | 0.19 ± 0.04 |

Example 12: Influence of Composition on CoF (Ratio PVP:PEI-g-PFPA:Castor Oil) and Wear To optimize the coating properties in terms of slipperiness (both wet and dry) and the dry appearance (not oily) several coating formulations were prepared as shown in Table 6. Polyester cover slips (Thermanox) were plasma cleaned for 2 min, and spray coated with coating formulations shown in Table 6. Coatings were cured under UV for 2 min at 3-4 mW/cm$^2$ UV flux at 254 nm. The appearance of the coatings was tested by placing a piece of aluminum foil on the sample, which was firstly pressed down with a pressure of approximately 26 MPa and then removed from the disk surface. The oiliness was qualitatively judged by ranking the amount of oil transferred from the coating to the foil. Coatings started to become oily above a Castor oil to PVP ratio of 0.6.

The frictional properties were evaluated in three different positions on each sample, first in the dry state, and in phosphate buffered saline. The coefficient of friction was calculated from a normal force ramp between 400-1200 mN against a PDMS pin with radius 2.5 mm. The results are shown in FIG. 3. The CoF when dry was very high with <3 mg/ml CO, and decreased until 10 mg/ml, after which the CoF was steadily below 0.04.

Additionally, the Solution No. 4-6 were tested for wear resistance in the dry state. The PDMS pin was slid back and forth 50 times whilst continuously recording the friction force, see FIG. 4. With increasing amount of CO in the coating formulation, the wear resistance of the coating increases.

TABLE 6

Prepared coating formulations.

| Solution no. | conc. of PEI-g-PFPA [mg/mL] | conc. of PVP [mg/mL] | conc. of lubricant [mg/mL] | PVP to PEI-g-PFPA m/m ratio | Castor oil to PVP ratio |
|---|---|---|---|---|---|
| 1 | 5 | 25 | 0 | 5 | 0 |
| 2 | 5 | 25 | 1.5 | 5 | 0.06 |
| 3 | 5 | 25 | 2 | 5 | 0.08 |
| 4 | 5 | 25 | 3 | 5 | 0.12 |
| 5 | 5 | 25 | 5 | 5 | 0.2 |
| 6 | 5 | 25 | 10 | 5 | 0.4 |
| 7 | 5 | 25 | 15 | 5 | 0.6 |
| 8 | 5 | 25 | 20 | 5 | 0.8 |

Example 13: Influence on Coating Thickness on Dry Lubricity

To evaluate the influence of coating thickness on CoF, a series of solutions were prepared having the same ratios of matrix:cross-linker:lubricant, but at different absolute concentrations, see Table 7. The thickness for the coating No 2 was approximately 500 nm, and for coating No 3, 1500 nm. The CoF was evaluated dry against PDMS pin (R=2.5 mm) between 400-1200 mN, see FIG. 5. No influence on coating thickness down to at least 500 nm could be detected.

TABLE 7

Prepared coating formulations.

| Solution no. | conc. of PEI-g-PFPA [mg/mL] | conc. of PVP [mg/mL] | conc. of lubricant [mg/mL] | PVP to PEI-g-PFPA m/m ratio | Castor oil to PVP ratio |
|---|---|---|---|---|---|
| 1 | 1 | 5 | 2 | 5 | 0.4 |
| 2 | 2 | 10 | 4 | 5 | 0.4 |
| 3 | 5 | 25 | 10 | 5 | 0.4 |
| 4 | 10 | 50 | 20 | 5 | 0.4 |

Example 14: Production of Coating Formulations with Different Ratios of Hydrophilic Polymer and Cross-Linker where Lubricant can be Added after Curing A solution of high molecular weight polyvinylpyrrolidone (PVP K94, Aldrich 437190) in ethanol with a concentration of 200 mg/mL is prepared. This solution can be mixed with different amounts of PEI-g-PFPA (10 mg/mL), PEI-g-salicylate (10 mg/mL) and ethanol to obtain coating formulations that have different viscosities depending on total concentration and lead to different crosslink densities and fluorescent properties after curing of the applied coating. Table 8 provides a few examples of solutions prepared this way.

TABLE 8

Examples of different coating formulations in ethanol prepared as described in Example 14 without containing an additional lubricant

| solution no. | conc. of PEI-g-PFPA [mg/mL] grafting ratio = 6 | conc. of PVP [mg/mL] | conc. of PEI-g-salicylate [mg/mL] | PVP to PEI-g-PFPA m/m ratio | PEI-g-salicylate to PEI-g-PFPA m/m ratio |
|---|---|---|---|---|---|
| 1 | 1 | 50 | — | 50 | |
| 2 | 0.5 | 25 | — | 50 | |
| 3 | 0.2 | 10 | — | 50 | |
| 4 | 2.5 | 50 | — | 20 | |
| 5 | 1.25 | 25 | — | 20 | |
| 6 | 0.5 | 10 | — | 20 | |
| 7 | 5 | 50 | — | 10 | |
| 8 | 2.5 | 25 | — | 10 | |
| 9 | 1 | 10 | — | 10 | |
| 10 | 10 | 50 | — | 5 | |
| 11 | 5 | 25 | — | 5 | |
| 12 | 2 | 10 | — | 5 | |
| 13 | 0.5 | 25 | 2.5 | 50 | 5 |
| 14 | 0.375 | 18.75 | 1.875 | 50 | 5 |
| 15 | 0.75 | 37.5 | 3.75 | 50 | 5 |
| 16 | 0.75 | 37.5 | 0 | 50 | 0 |
| 17 | 0.375 | 18.75 | 1.875 | 50 | 5 |
| 18 | 0 | 18.75 | 1.875 | | |
| 19 | 0.75 | 18.75 | 1.875 | 25 | 2.5 |
| 20 | 0.75* | 18.75 | 1.875 | 25 | 2.5 |
| 21 | 0.25 | 12.5 | 1.25 | 50 | 5 |
| 22 | 0.2 | 10 | 1 | 50 | 5 |
| 23 | 0.125 | 6.25 | 0.625 | 50 | 5 |

*grafting ratio of PEI-g-PFPA is 12

Example 15 Tribological Performance of Coatings with Low Molecular Weight PEG in the Liquid as Viscosity Modifier in Harsh Contact Conditions (150 MPa Contact Pressure)

Silicon wafers (2×1 cm) were sonicated (2×10 min Toluene, 2×10 min IPA), rinsed and dried with a stream of nitrogen. Subsequently samples were spray coated with solution 2 of Table 8. Dry film thickness of 80 and 200 nm were produced by application of different amounts of coating formulation.

The covalent attachment and cross-linking was triggered by activating the PFPA by UV irradiation (2 min, lambda=254 nm, 800 µW/cm2). The coated samples were rinsed with pure water thereafter to remove potentially unbound species.

Coated samples were evaluated with respect to coefficient of friction during tribological testing. Ratio of water and PEG (400 g/mol) confined in the coating was varied between 0 and 100%, with 0 being pure water and 100% being pure PEG (FIG. 6).

Specifically, the time-scales associated with the onset of wear are controlled by the design of the coating in terms of poroviscoelastic properties (mesh size, permeability, modulus, viscosity, thickness) with respect to the final contact conditions it is exposed to. FIG. 7 shows how adjusting the viscosity of the solution allows one to adapt the squeeze-out time of the coating to match the migration time of the tribological contact.

Example 16 Application of an Optional Adhesion Layer on a Single Use Polypropylene Intraocular Lens Delivery Device for Cataract Surgery (PP IOL Device)

Samples are treated with oxygen plasma for 8 minutes and dipped in a solution of PEI-g-PFPA in ethanol with a concentration of 0.5 mg/mL for 3 minutes. The samples are dried by spinning in a centrifuge and stored in the dark until further coating.

Example 17 Application of Coating Formulation Inside a PP IOL Device

Devices, with or without optional adhesion layer, are coated by filling and emptying with solution 14 of Table 8 leaving behind a thin film of the coating formulation inside the device that its air dried. Alternatively, the coating can be applied by jetting, spraying, dip-coating printing or painting.

Example 18 Curing of Applied Coatings Inside a PP IOL Device

Devices are placed in a UV-C chamber at an intensity of 6 mW/cm$^2$ for 2-12 minutes. Optionally, in case the material is stable, samples can be cured thermally at a temperature above 120° C. for 1 hour or 160° C. for 5 minutes.

Samples can be optionally washed by immersion in water to remove non-bound parts of the coating. Increasing the UV illumination time reduces the loss of unbound polymer after rinsing. Also, particles generated during injection of the intraocular lens are reduced.

Example 19 Testing Injection Force of Coated PP IOL Device

Implant lenses were placed together with a drop of water containing a lubricant (sodium hyaluronate) into the channel of the device and then injected through the device, while recording the injection force. A significant reduction of the maximum force needed compared to uncoated devices is measured when coating formulation 14 of Table 8 is used. CoF slightly increases with increasing illumination time (10 versus 3 minutes). Without PEI-g-PFPA (solution 18 of Table 8), the coating does not adhere to the surface and injection force is as high as for the uncoated sample. Reducing the coating thickness reduces the lubricity (solution 23 versus solution 14 of Table 8).

Example 20 Coating of Soft Contact Lenses

Silicone-hydrogel contact lenses were rinsed in ultra-pure water, and mounted on a rounded sample holder with the same internal diameter as the lens. The lens was dried with a stream of $N_2$ gas. An adhesion primer of PEI-g-PFPA was sprayed over the entire lens surface from a 0.1 mg/ml dilution in ethanol. A coating formulation having 10 mg/ml PVP, and 1 mg/ml of cross-linker described in solution 9 of Table 8 in ethanol was applied by spray coating over the entire lens surface. After drying, the coating was cured for 2 min at 3-4 mW/cm$^2$ UV flux at 254 nm. Lenses were immersed in phosphate buffered saline over night at 4° C. Friction testing of coated and uncoated lenses were performed using a a simulated tear solution described in Sterner, O.; Aeschlimann, R.; Zürcher, S.; Lorenz, K. O.; Kakkassery, J.; Spencer, N. D.; Tosatti, S. G. P. Friction Measurements on Contact Lenses in a Physiologically Relevant Environment: Effect of Testing Conditions on FrictionFriction Measurements on Contact Lenses. *Investigative Ophthalmology & Visual Science* 2016, 57 (13), 5383-5392. This solution is containing different lipids and mucin as in natural tears and acts as a viscosity modifier and lubricant.

CoF values for coated and uncoated lenses are shown in FIG. 8. The coated lens had a 10 times reduction in CoF compared with the uncoated lens.

The invention claimed is:
1. A device comprising a lubricating coating directly on its surface for use in wet and dry conditions, wherein the lubricating coating comprises
   i. at least one polymer A selected from the group consisting of polyvinylpyrrolidone (PVP), linear or branched polyethyleneglycol (PEG), dextran, polyalkyloxazolines (PAOXA), poly(2-methyl-2-oxazoline) (PMOXA), poly(ethyl-oxazoline) (PEOXA), hyaluronic acid, polyvinylalcohol (PVA), poly(2-hydroxyethyl methacrylate) (pHEMA), poly(1-vinylpyrrolidone-co-styrene), poly(1-vinylpyrrolidone)-graft-(1-triacontene), poly(1-vinylpyrrolidone-co-vinyl acetate), poly(ethylene-co-vinyl alcohol), poly(ethylene-co-vinyl-pyrrolidone), poly(maleic acid), poly(ethylene-co-maleic acid), polyacrylic acid, poly(acrylamide), poly[N-(2-hydroxypropyl) methacrylamide] (PHPMA), poly(N-isopropylacrylamide) (PNIPAM), poly[(organo)phosphazenes], chitosan and its derivatives, xantham gum, starch, pectin, algin, agarose, cellulose and its derivatives or a mixture thereof,
   ii. at least one cross-linker comprising a core and at least two reactive groups, wherein:
      the core is selected from the group consisting of polyallylamine (PAAm), polyethylene glycol (PEG), polyvinylpyrrolidone (PVP), polyethyleneimine (PEI), polylysine (PLL), polyacrylic acid (PAA), polyvinylalcohol (PVA), polyaspartic acid, dextran, chitin, chitosan, agarose, albumin, fibronectin, fibrinogen, keratin, collagen, lysozyme and multivalent molecules having less than 20 carbon atoms, the reactive groups are each independently selected from the group consisting of

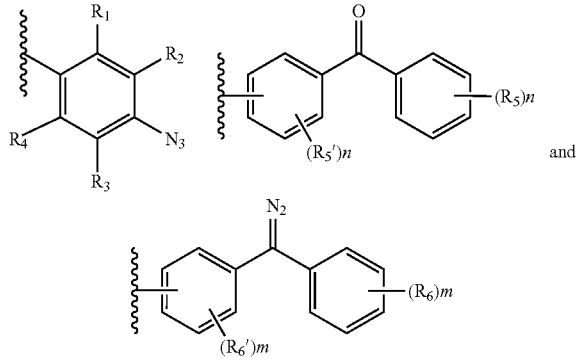

and mixtures thereof, wherein:

$R_1$, $R_2$, $R_3$ and $R_4$ are, independently from one another, H, F or Cl;

$R_5$ and $R_5'$ is independently methyl, ethyl, propyl, isopropyl or dimethylamine and n is 0 to 4, and $R_6$ and $R_6'$ is independently methyl, ethyl, propyl, isopropyl or dimethylamine and m is 0 to 4, and the core is linked to the reactive group by a linker group B selected from the group consisting of a secondary or tertiary amine, an ether, a thioether, a carboxylic acid ester, an amide and a thioester, and iii. at least one lubricant which is a synthetic oil or at least one member selected from the group consisting of an edible oil, a fat from plants, a fat from animals, a lipid and a hyaloronate, wherein:

a portion of the at least two reactive groups of the cross-linker are covalently linked to the polymer A to form a three-dimensional network in which the lubricant is incorporated, and at the same time another portion of the reactive groups of the cross-linker are covalently linked to the surface of the device.

2. The device according to claim 1 wherein the core of the at least one cross-linker is polyallylamine (PAAm), polyvinylpyrrolidone (PVP) or polyethyleneimine (PEI).

3. The device according to claim 1, wherein the core of the at least one cross-linker is a multivalent molecule having less than 20 carbon atoms.

4. The device according to claim 1, wherein the device is a medical device.

5. The device according to claim 1, wherein the coating comprises at least two different cross-linkers.

6. The device according to claim 1, wherein the cross-linker is selected from the group consisting of polyethyleneimine-grafted-perfluorophenylazide (PEI-g-PFPA), tris (2-PFPA-aminoethyl)amine and 2,2'-(ethylenedioxy)bis (ethylamine-PFPA).

7. The device according to claim 1, wherein the three-dimensional network further comprises a fluorescent marker.

8. The device according to claim 1, wherein the coating is free from UV-radical initiators.

9. A method for producing a device according to claim 1, by a. preparing a coating formulation comprising the at least one polymer A, the at least one cross-linker and at least one solvent, b. applying the coating on the surface of the device, c. forming a three-dimensional network and simultaneously linking the network to the surface of the device by radiation or/and by heat, wherein the lubricant which is a synthetic oil or at least one member selected from the group consisting of an edible oil, a fat from plants, a fat from animals, a lipid and a hyaloronate is added to the coating formulation or after the formation of the three-dimensional network.

10. The method according to claim 9, wherein the coating formulation comprises the lubricant.

11. The method according to claim 9, wherein the coating is applied by jetting, spraying, dip-coating, printing, painting or filling and emptying.

12. A method comprising operating the device according to claim 1 in dry and in wet conditions.

13. A device comprising a lubricating coating directly on its surface for use in dry conditions, wherein the lubricating coating comprises i. at least one polymer A selected from the group consisting of polyvinylpyrrolidone (PVP), linear or branched polyethyleneglycol (PEG), dextran, polyalkyloxazolines (PAOXA), poly(2-methyl-2-oxazoline) (PMOXA), poly(ethyl-oxazoline) (PEOXA), hyaluronic acid, polyvinylalcohol (PVA), poly(2-hydroxyethyl methacrylate) (pHEMA), poly(1-vinylpyrrolidone-co-styrene), poly(1-vinylpyrrolidone)-graft-(1-triacontene), poly(1-vinylpyrrolidone-co-vinyl acetate), poly(ethylene-co-vinyl alcohol), poly(ethylene-co-vinyl-pyrrolidone), poly(maleic acid), poly(ethylene-co-maleic acid), polyacrylic acid, poly(acrylamide), poly[N-(2-hydroxypropyl) methacrylamide] (PHPMA), poly(N-isopropylacrylamide) (PNIPAM), poly[(organo)phosphazenes], chitosan and its derivatives, xantham gum, starch, pectin, algin, agarose, cellulose and its derivatives or a mixture thereof, ii. at least one cross-linker comprising a core and at least two reactive groups, wherein:

the core is selected from the group consisting of polyallylamine (PAAm), polyethylene glycol (PEG), polyvinylpyrrolidone (PVP), polyethyleneimine (PEI), polylysine (PLL), polyacrylic acid (PAA), polyvinylalcohol (PVA), polyaspartic acid, dextran, chitin, chitosan, agarose, albumin, fibronectin, fibrinogen, keratin, collagen, lysozyme and multivalent molecules having less than 20 carbon atoms, the reactive groups are each independently selected from the group consisting of

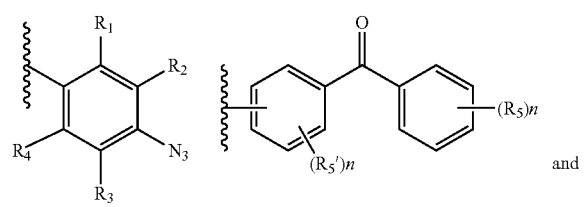

and

-continued

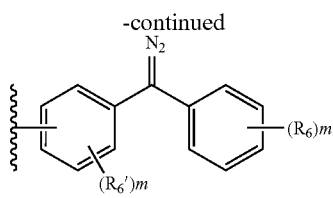

and mixtures thereof, wherein:
- $R_1$, $R_2$, $R_3$ and $R_4$ are, independently from one another, H, F or Cl;
- $R_5$ and $R_5'$ is independently methyl, ethyl, propyl, isopropyl or dimethylamine and n is 0 to 4, and
- $R_6$ and $R_6'$ is independently methyl, ethyl, propyl, isopropyl or dimethylamine and m is 0 to 4, and the core is linked to the reactive group by a linker group B selected from the group consisting of a secondary or tertiary amine, an ether, a thioether, a carboxylic acid ester, an amide and a thioester, and iii. at least one lubricant which is a synthetic oil or at least one member selected from the group consisting of an edible oil, a fat from plants, a fat from animals, a lipid and a hyaloronate, wherein:
a portion of the at least two reactive groups of the cross-linker are covalently linked to the polymer A to form a three-dimensional network in which the lubricant is incorporated, and at the same time another portion of the reactive groups of the cross-linker are covalently linked to the surface of the device.

14. A method comprising operating the device according to claim 13 in dry conditions.

15. The device according to claim 1, wherein the lubricant is the edible oil.

16. The device according to claim 1, wherein the lubricant is the fat from plants.

17. The device according to claim 1, wherein the lubricant is the fat from animals.

18. The device according to claim 1, wherein the lubricant is the lipid.

19. The device according to claim 1, wherein the lubricant is the hyaloronate.

20. The device according to claim 1, wherein the cellulose derivatives comprise at least one selected from the group consisting of cellulose esters, cellulose ethers, hydroxypropylmethyl cellulose (HPMC), and hydroxyethyl cellulose (HEC).

21. The device according to claim 13, wherein the cellulose derivatives comprise at least one selected from the group consisting of cellulose esters, cellulose ethers, hydroxypropylmethyl cellulose (HPMC), and hydroxyethyl cellulose (HEC).

* * * * *